(12) United States Patent
Milan

(10) Patent No.: US 9,181,008 B2
(45) Date of Patent: Nov. 10, 2015

(54) TEMPERATURE-SENSITIVE PACKAGING CLOSURES

(75) Inventor: Guy Dimitri Milan, Woodbridge (GB)

(73) Assignee: Milan Innovation Ltd., Woodbridge, Suffolk (GB)

( * ) Notice: Subject to any disclaimer, the term of this patent is extended or adjusted under 35 U.S.C. 154(b) by 660 days.

(21) Appl. No.: 13/501,612

(22) PCT Filed: Oct. 8, 2010

(86) PCT No.: PCT/GB2010/051699
§ 371 (c)(1),
(2), (4) Date: Apr. 12, 2012

(87) PCT Pub. No.: WO2011/045586
PCT Pub. Date: Apr. 21, 2011

(65) Prior Publication Data
US 2012/0238950 A1 Sep. 20, 2012

(30) Foreign Application Priority Data

Oct. 13, 2009 (GB) .................................. 0917887.2
Feb. 2, 2010 (GB) .................................. 1001705.1
Jul. 8, 2010 (GB) .................................. 1011498.1

(51) Int. Cl.
*B65D 51/24* (2006.01)
*B65D 79/02* (2006.01)
(Continued)

(52) U.S. Cl.
CPC ............... *B65D 51/24* (2013.01); *B65D 79/02* (2013.01); *G01K 3/00* (2013.01); *G01K 5/02* (2013.01);
(Continued)

(58) Field of Classification Search
CPC ....... A61M 5/31; A61M 5/50; A61M 5/5013; A61M 2005/5033; A61M 5/32
USPC ................... 604/82, 181, 187, 110, 111, 192, 604/193–195, 208
See application file for complete search history.

(56) References Cited

U.S. PATENT DOCUMENTS 3,017,763 A 1/1962 Weil
3,464,414 A * 9/1969 Sponnoble .................... 206/221
(Continued)

FOREIGN PATENT DOCUMENTS

DE 42 05 403 A1 8/1993
FR 2 887 646 A1 12/2006
(Continued)

OTHER PUBLICATIONS

Atkinson, W. L., Pickering, L. K., Schwartz, B., Weniger, B. G., Iskander, J. K., & Watson, J. C. (2002). General recommendations on immunization. Recommendations of the Advisory Committee on Immunization Practices (ACIP) and the American Academy of Family Physicians (AAFP) MMWR Recomm Rep, 51, 1-35.*
(Continued)

*Primary Examiner* — Kami A Bosworth
*Assistant Examiner* — Nilay Shah
(74) *Attorney, Agent, or Firm* — Hayes Soloway PC

(57) ABSTRACT

A device containing a temperature-sensitive material comprises a first part containing the material, a second part which engages the first part and allows, or can be disengaged or displaced to allow, the material to be dispensed or utilised, a locking means, and a temperature-sensitive activator for the locking means that is activated at a predetermined temperature, and thereby irreversibly prevents the material from being dispensed or utilised should it become frozen or exposed to temperatures below a predetermined limit.

13 Claims, 12 Drawing Sheets

(51) Int. Cl.
*G01K 3/00* (2006.01)
*G01K 5/02* (2006.01)
*G01K 5/14* (2006.01)
*G01K 5/48* (2006.01)
*G01K 5/62* (2006.01)
*G01K 11/06* (2006.01)
*A61M 5/30* (2006.01)
*A61M 5/31* (2006.01)
*A61M 5/32* (2006.01)

(52) U.S. Cl.
CPC ........... *G01K 5/14* (2013.01); *G01K 5/483* (2013.01); *G01K 5/62* (2013.01); *G01K 11/06* (2013.01); *A61M 5/30* (2013.01); *A61M 5/31* (2013.01); *A61M 5/32* (2013.01)

(56) References Cited

U.S. PATENT DOCUMENTS

| | | | |
|---|---|---|---|
| 4,298,143 A | | 11/1981 | Peterson |
| 4,361,408 A | | 11/1982 | Wirtschafter |
| 4,801,295 A | | 1/1989 | Spencer |
| 4,995,874 A | * | 2/1991 | Strickland ............... 604/195 |
| 5,076,197 A | | 12/1991 | Darringer et al. |
| 5,129,536 A | | 7/1992 | Robinson |
| 5,457,665 A | | 10/1995 | Reid |
| 5,690,942 A | * | 11/1997 | Hjorth ............... 424/283.1 |
| 5,826,715 A | | 10/1998 | Thompson |
| 6,062,126 A | | 5/2000 | Johnson et al. |
| 6,190,364 B1 | * | 2/2001 | Imbert ............... 604/256 |
| 6,267,749 B1 | * | 7/2001 | Miklos et al. ............... 604/110 |
| 6,401,991 B1 | | 6/2002 | Eannone |
| 7,343,872 B2 | * | 3/2008 | Taylor et al. ............... 116/216 |
| 7,680,001 B1 | | 3/2010 | D'Annunzio et al. |
| 2003/0090364 A1 | | 5/2003 | Cardinale et al. |
| 2004/0019453 A1 | | 1/2004 | Blakley |
| 2009/0088724 A1 | * | 4/2009 | Chebator et al. ............... 604/508 |
| 2011/0121023 A1 | | 5/2011 | Milan |

FOREIGN PATENT DOCUMENTS

| | | | |
|---|---|---|---|
| FR | 2 896 311 A1 | | 7/2007 |
| GB | 1 370 989 A | | 10/1974 |
| GB | 2 199 016 A | | 6/1988 |
| GB | 2 358 178 A | | 7/2001 |
| GB | 2 378 941 A | | 2/2003 |
| GB | 2 459 317 A | | 10/2009 |
| WO | WO 9947194 A1 | * | 9/1999 |
| WO | 02/42179 A1 | | 5/2002 |
| WO | 02/056820 A1 | | 7/2002 |
| WO | WO 02056820 A1 | * | 7/2002 |
| WO | 2004/013591 A1 | | 2/2004 |
| WO | 2005/020168 A2 | | 3/2005 |
| WO | 2006/077087 A2 | | 7/2006 |

OTHER PUBLICATIONS

International Search Report for application PCT/GB2009/050368, having a mailing date of Aug. 18, 2009.
Preliminary Report for parent application PCT/GB2010/051699, having a completion date of Jan. 18, 2012.
Applicant's Reply to Written Opinion dated Oct. 26, 2011 in parent application PCT/GB2010/051699, dated Dec. 16, 2011.

* cited by examiner

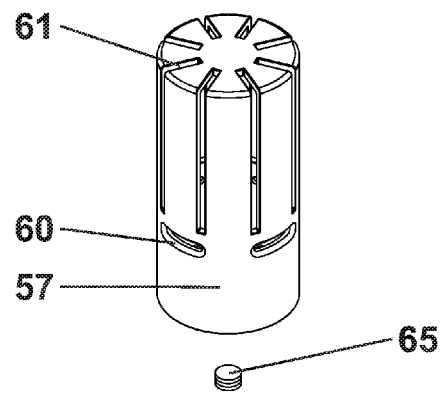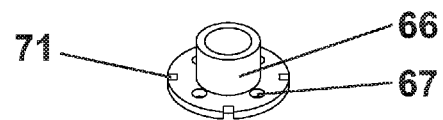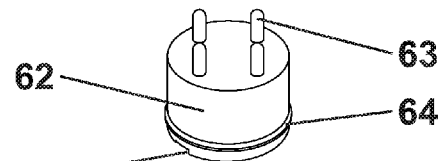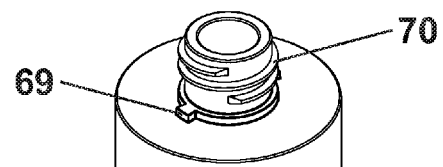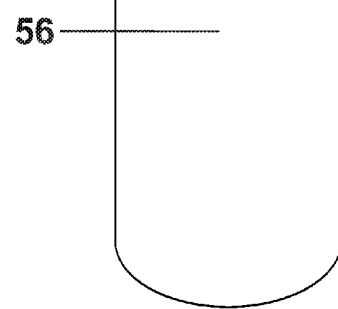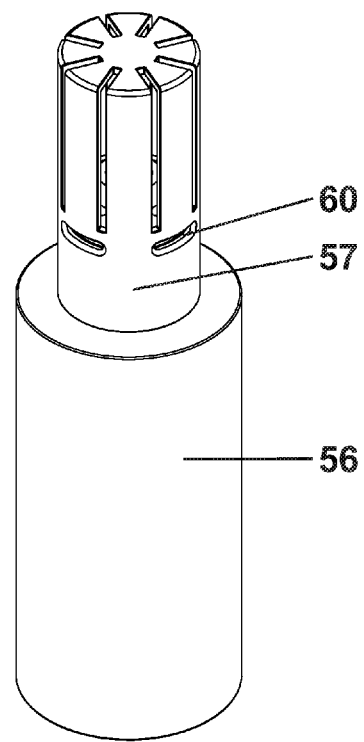
Figure 12                    Figure 13

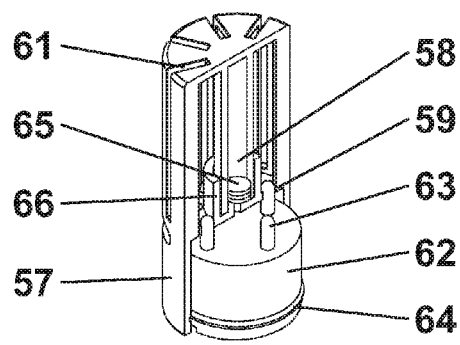
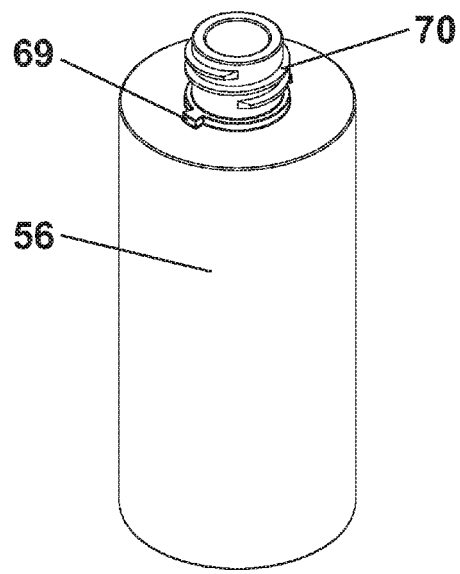
Figure 14
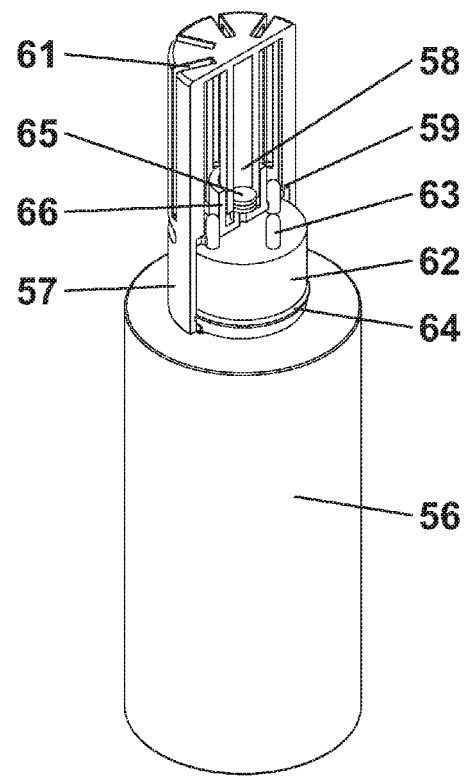
Figure 15

TEMPERATURE-SENSITIVE PACKAGING CLOSURES

CROSS-REFERENCE TO RELATED APPLICATIONS

This application is the U.S. national stage application of International Application No. PCT/GB2010/051699, filed Oct. 8, 2010, which International application was published on Apr. 21, 2011 as International Publication No. WO 2011/045586 A2 in the English language and which application is incorporated herein by reference. The International application claims priority of Great Britain Patent Application No. 0917887.2, filed Oct. 13, 2009, Great Britain Patent Application No. 1001705.1, filed Feb. 2, 2010, and Great Britain Patent Application No. 1011498.7, filed Jul. 8, 2010, which applications are incorporated herein by reference.

FIELD OF THE INVENTION

The present invention relates to the packaging of certain pharmaceutical products and other non-durable products, the quality and efficaciousness of which deteriorate when frozen or exposed to temperatures below a predetermined limit.

BACKGROUND OF THE INVENTION

The quality and efficaciousness and in some instances safety of certain pharmaceutical products and other non-durable products deteriorate when frozen or exposed to temperatures below a predetermined limit. Certain vaccines, if frozen, suffer a loss of potency which cannot be restored, thereby diminishing the effectiveness of the vaccine and increasing the risk of adverse events, such as sterile abscesses, following immunization. Vaccines damaged by freezing include Diphtheria Toxoid, Hepatitis A, Hepatitis B, Influenza, Liquid Hib Conjugate, Pertussis, Pneumococcal Conjugate, Poliovirus (inactivated), Tetanus Toxoid, Typhoid (inactivated) and combinations containing these vaccines. Other pharmaceutical products, including insulin and certain morphine suspensions for injection, are also damaged by freezing. The freezing point for a given vaccine or other pharmaceutical product is dependent on a number of factors including temperature, rate of temperature change, duration of exposure, supercooling effects and vibration.

A number of indicators have become available that undergo a colour change when exposed to freezing temperatures. FREEZEmarker®, produced by the Temptime Corporation (USA), and Freeze Watch™, produced by the 3M Corporation (USA), are label-type devices designed to be affixed to or placed within the packaging for products that can be damaged when exposed to freezing temperatures and inform the user, by means of a colour change, if a freeze event has occurred. Freeze-tag produced by Berlinger and Company AG (DE) and FreezeAlert produced by Sensitech Inc (USA) are battery operated electronic temperature monitoring devices that inform the user, by means of an electronic display, if a freeze event has occurred. Freeze indicators of these types are designed to activate, subject to a tolerance of accuracy, at a predetermined temperature in line with the assumed freezing point of the vaccine or other pharmaceutical product with which they are to be packaged. However, they do not take into account factors such as rate of temperature change, supercooling effects and vibration that may affect the freezing point of the vaccine or other pharmaceutical product. They also suffer the disadvantage that the user is relied upon to correctly interpret and act in accordance with the indication provided.

To ensure product quality and efficacy and to safeguard the health and safety of consumers, a need therefore exists to prevent the use of certain nondurable products if frozen or exposed to temperatures below a predetermined limit.

WO2006/077087 discloses a device for dispensing ice cream. The device comprises a container having an aperture through which material in the container can be dispensed, a closure for the aperture that is biased by a spring into a closed position, and a connecting temperature-sensitive element that is rigid below a predetermined temperature, whereby the closure can be opened, and non-rigid above that temperature, so that the element does not connect the container and the closure and the latter cannot be opened. This effect is designed to be reversible.

WO02/056820 discloses a closure cap apparatus for a medicament container. The device comprises a container having an aperture through which material in the container can be dispensed and a closure for the aperture which utilises the change in shape of a shape-memory-alloy from a second shape to a first shape to prevent access to the contents of the container should the container be exposed to a temperature above a predetermined limit. The effect is designed to be irreversible but does not prevent access to the contents of a container which deteriorate when frozen or exposed to temperatures below a predetermined limit.

SUMMARY OF THE INVENTION

According to the present invention, a device containing a temperature-sensitive material, comprises a first part containing the material and a second part which engages the first part and allows, or can be disengaged or displaced to allow, the material to be dispensed or utilised, a locking means, and a temperature-sensitive activator for the locking means that is activated at a predetermined temperature and thereby irreversibly prevents the material from being dispensed or utilised should it become frozen or exposed to temperatures below a predetermined limit. The device may include, as desired, a visual indication of the state of the locking means.

The first part may comprise one or more apertures which allow material to be dispensed. The, or one such, aperture may provide for connection with the second part.

A particular advantage of the present invention is that, rather than relying on the end user to correctly identify and act in accordance with an indicating device that may be attached to a product package, the locking system of the invention physically prevents the product from being dispensed from or utilised within the package once the contents of the package have been frozen or exposed to temperatures below a predetermined limit.

BRIEF DESCRIPTION OF THE DRAWINGS

FIG. 12 shows, in perspective, the constituent parts of a product package consisting of a container with a screw cap incorporating a freeze-sensitive locking system with visual indicator.

FIG. 13 shows, in perspective, the assembled product container.

FIG. 14 shows, in perspective, with outer cap in section, the open product container. FIG. 15 shows, in perspective, with outer cap in section, the container and screw cap locked together by means of the freeze-sensitive locking system.

DESCRIPTION OF PREFERRED EMBODIMENTS

Figure 1:
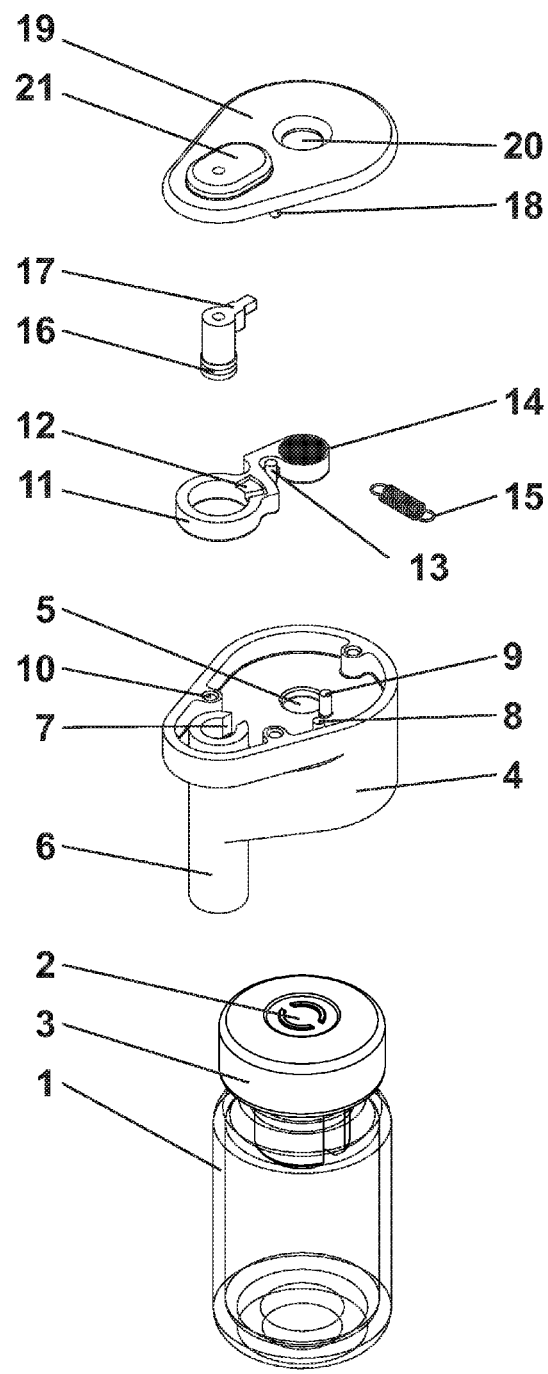
FIG. 1 shows, in perspective, the constituent parts of a pharmaceutical product vial with a secondary cap containing a freeze-sensitive locking system.

The first part of a device of the invention may take any suitable form such as a syringe barrel or a container for a liquid or dry substance or other consumable product. Examples of materials that may be contained within the first part will be well known to those of ordinary skill in the art. They include pharmaceutical and medical products, e.g. vaccines, insulin etc. The material may be in a single piece or discrete pieces. Depending on the nature of the material, means may be provided for its advancement through an aperture in the first part, whereby the user gains ready access to a further supply of the material or an applicator or other means may be provided to enable the material to be accessed and/or applied or used by the user.

The second part of a device of the invention may take any suitable form such as a syringe plunger, screw cap, hinged lid, valve, moveable plate or other closure for a container. The second part may be provided with a means, such as a ratchet in the case of a screw cap or hinged lid, to enable the second part to be reengaged or replaced should the first and second parts be disengaged or displaced when the temperature-dependant locking system is activated.

A preferred embodiment of the invention is a syringe. The syringe barrel may provide the first part of the device. Alternatively, the first part may be a vial or other container having a sealed opening through which a syringe needle can be passed. In such a device (as illustrated below in the first embodiment), access to the first part can be prevented, e.g. by a moveable plate whose effect is to irreversibly prevent the syringe needle from passing through the aperture.

A syringe barrel, locking step and upper barrel may be manufactured as a single unit by means of injection-moulding (as illustrated below in the third embodiment) or may be produced by the joining of two or more separate components manufactured from the same or different materials such as a glass syringe barrel attached to an injection-moulded plastic upper barrel (as illustrated below in the fifth embodiment) for example.

A syringe barrel and plunger rod assembly may include a means to prevent re-use of the syringe such as a two-part plunger rod which prevents the plunger from travelling back up the syringe barrel after administration of the syringe contents (as illustrated below in the third embodiment) or a needle retraction system (as illustrated below in the fifth embodiment) which not only prevents re-use of the syringe after the contents have been administered but also prevents needle stick injury.

A syringe barrel may also include means to facilitate mixing of the syringe contents prior to administration such as an annular piece 99 placed in the syringe barrel which is free to travel through the contents of the syringe and which is so configured as to allow the contents to pass freely through the syringe needle upon administration.

The spring arms on the lower plunger rod may form an integral part of the lower plunger rod (as shown in the third and fifth embodiments) or may be provided by means of injection-moulding the lower plunger rod over a cantilever spring arrangement produced from the same or a different material, or by attaching, by any suitable means, a cantilever spring arrangement produced from the same or a different material to the lower plunger rod. The function of the spring arms is to prevent the lower plunger rod from travelling down the syringe barrel upon freezing of the contents of the syringe barrel and may be provided by any suitable arrangement such as an 'O' ring, a polymer jacket energised by a metallic spring or any other suitable spring element or elements formed on, or attached to, the lower plunger rod which, when released by the syringe barrel, prevent the lower plunger rod from travelling down the syringe barrel.

The device includes a temperature-sensitive activator. For this purpose, measurement means within the device may be of any nature suitable for the measurement of temperature. For example, the measurement means may be of a mechanical nature such as a cylinder-and-piston arrangement containing water, an aqueous liquid optionally containing a colligative agent and or an ice-nucleating agent, a non-aqueous liquid, a liquid pharmaceutical preparation or any other liquid or solid component which expands upon freezing or contracts upon exposure to temperatures below a predetermined limit to provide a mechanical action or a bi-metal, bi-plastic, shape-memory-alloy or shape-memory-polymer component which converts a change in temperature into a mechanical displacement.

Alternatively, the measurement means within the device may be of an electrical-electronic nature such as a battery-operated electronic temperature monitoring circuit so configured as to operate a shape-memory-alloy actuator, solenoid or other electrical-mechanical device when a predetermined temperature is reached.

The locking means may be of any form suitable for preventing or enabling the disengagement or displacement of the first part relative to the second part, such as a movable latch so configured as to prevent or enable, in concord with the state of the measurement means, the relative rotation of a first annular piece about a second annular piece, or a moveable element so configured as to prevent or enable, in concord with the state of the measurement means, the unidirectional or bidirectional linear or rotary movement of a first piece with respect to a second piece.

The indicator of the device may be so arranged as to provide the user with feedback as to the state of the locking means before and after activation.

A first embodiment of the invention will now be described by way of example only with reference to FIGS. 1 to 4 of the accompanying drawings, in which:

FIG. 1 shows, in perspective, the constituent parts of a pharmaceutical product vial with a secondary cap containing a freeze-sensitive locking system.

Figure 2:
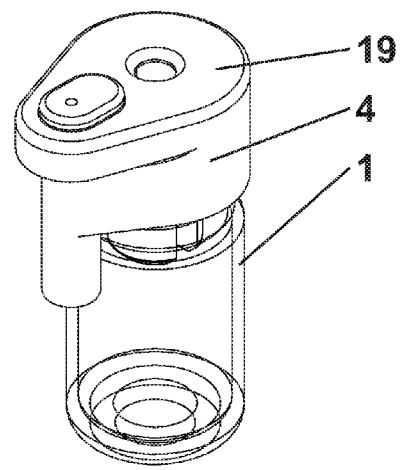
FIG. 2 shows, in perspective, the assembled pharmaceutical product vial with secondary cap containing a freeze-sensitive locking system.

FIG. 2 shows, in perspective, the assembled pharmaceutical product vial with secondary cap containing a freeze-sensitive locking system.

Figure 3:
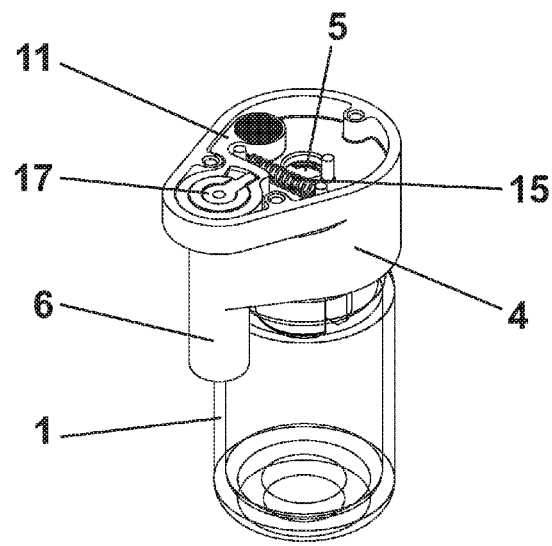
FIG. 3 shows, in perspective, the vial assembly with the secondary cap cover removed.

FIG. 3 shows, in perspective, the vial assembly with the secondary cap cover removed.

Figure 4:
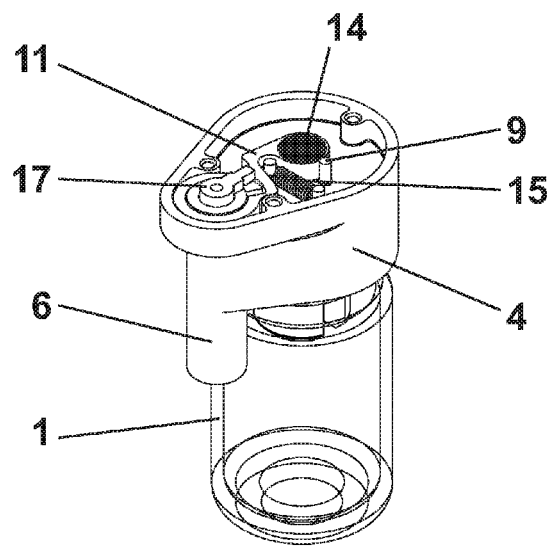
FIG. 4 shows, in perspective, the vial assembly with the secondary cap cover removed, after the assembly has undergone a freeze-thaw cycle.

FIG. 4 shows, in perspective, the vial assembly, with the secondary cap cover removed, after the assembly has undergone a freeze-thaw cycle.

With reference to FIGS. 1 to 4, the pharmaceutical product vial with a secondary cap containing a freeze-sensitive locking system comprises a vial 1 with rubber stopper 2 and metal crimp 3 attached, by means of an adhesive (not shown), to a secondary cap 4 with lower syringe needle aperture 5, actuator barrel 6, actuator guide 7, retaining pin 8, latch stop 9, and location pin recesses 10. Placed over, and free to rotate about the upper part of the actuator barrel 6 is a latch 11 with locking step 12, retaining pin 13 and indicator flag 14. Maintaining a clockwise biasing force on the latch 11 is a spring 15 which is secured to the secondary cap 4 and to the latch 11 by means of the retaining pins 8 and 13. Placed within the actuator barrel 6 is an actuator seal 16 to one end of which is attached an actuator arm 17 which is prevented from rotating relative to the longitudinal axis of the actuator barrel 6 by the actuator guide 7. Secured to the upper surface of the secondary cap 4 by means of location pins 18 and location pin recesses 10 is a cover 19 with upper syringe needle aperture 20 and actuator arm travel recess 21.

At assembly, the actuator barrel 6 is filled with a water solution (not shown) and sealed by the actuator seal 16. Clockwise rotation of the latch 11, under the force of the spring 15, is prevented by the actuator arm 17 engaging the locking step 12, thereby enabling the needle of a syringe to be passed through the upper syringe needle aperture 20 in the cover 19 and the lower syringe needle aperture 5 in the secondary cap 4 and hence through the rubber stopper 2 and into the vial 1, as shown in FIGS. 1 to 3.

Should the contents of the vial 1 freeze, the water solution contained by the actuator barrel 6, so formulated as to freeze at the same temperature as the contents of the vial 1, expands, thereby forcing the actuator seal 16 along the actuator barrel 6 and into the actuator arm travel recess 21, disengaging the actuator arm 17 from the locking step 12 and allowing the latch 11 to rotate clockwise about the longitudinal axis of the actuator barrel 6 under the force of the spring 15, until the latch 11 is prevented from rotating further by the latch stop 9 on the secondary cap 4 and the indicator flag 14 appears in the upper syringe needle aperture 20 thereby indicating to the user that the contents of the vial 1 have been frozen and irreversibly preventing the needle of a syringe from entering the vial 1, as shown in FIGS. 1, 2 and 4.

Figure 5:
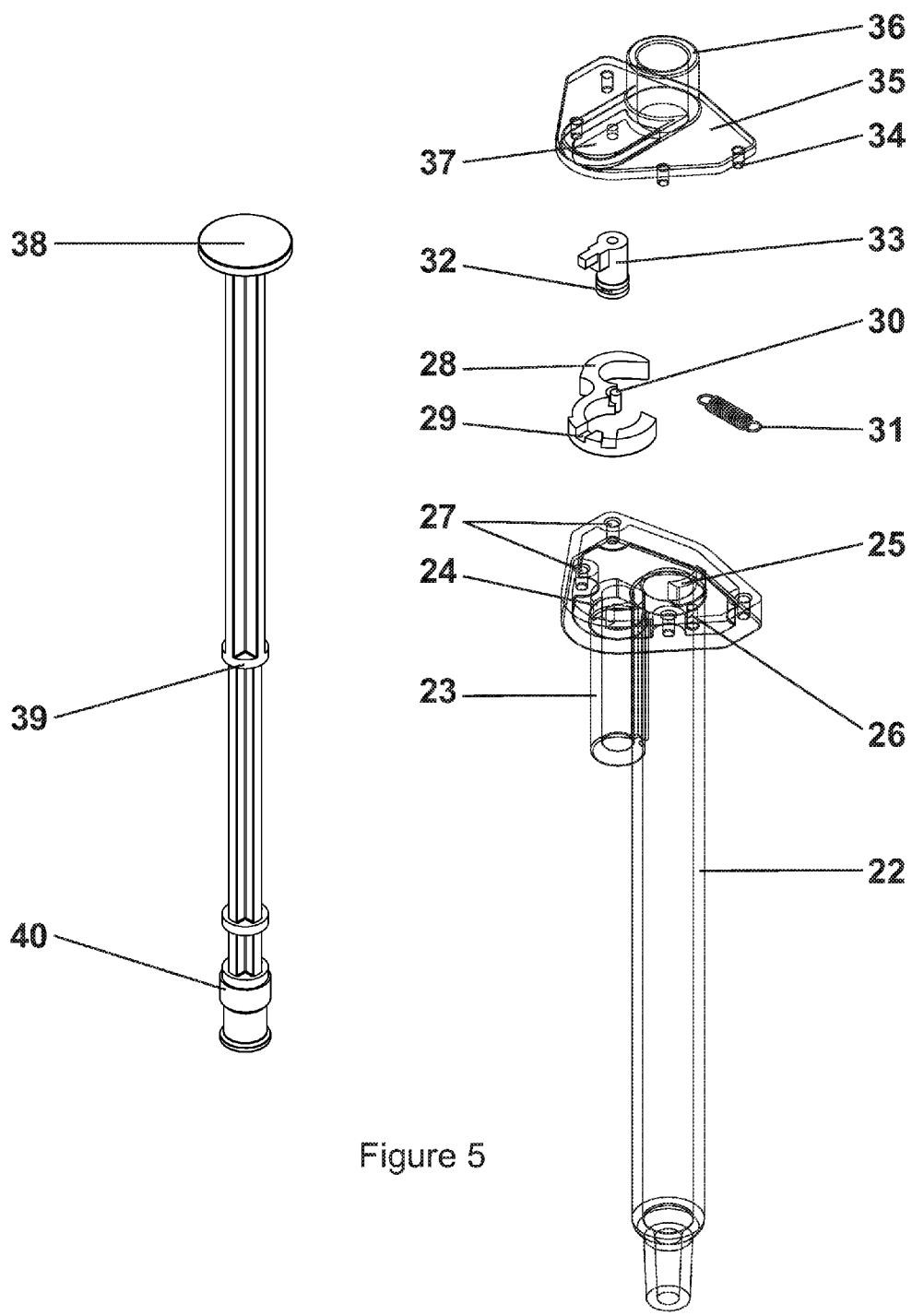
FIG. 5 shows, in perspective, the constituent parts of a pre-fillable syringe incorporating a freeze-sensitive locking system.

A second embodiment of the invention will now be described by way of example only with reference to FIGS. 5 to 8 of the accompanying drawings, in which:

FIG. 5 shows, in perspective, the constituent parts of a pre-fillable syringe incorporating a freeze-sensitive locking system.

Figure 6:
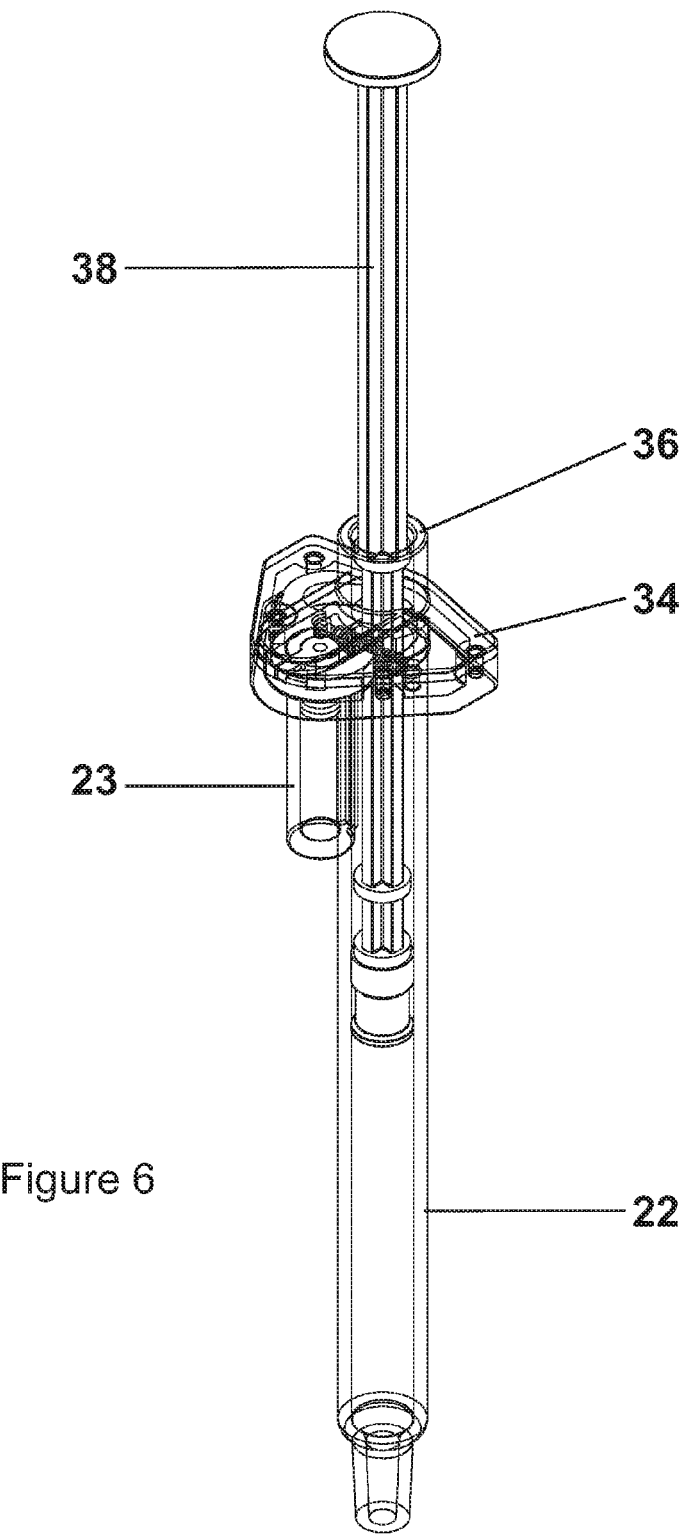
FIG. 6 shows, in perspective, the assembled pre-fillable syringe incorporating a freeze-sensitive locking system.

FIG. 6 shows, in perspective, the assembled pre-fillable syringe incorporating a freeze-sensitive locking system.

Figure 7:
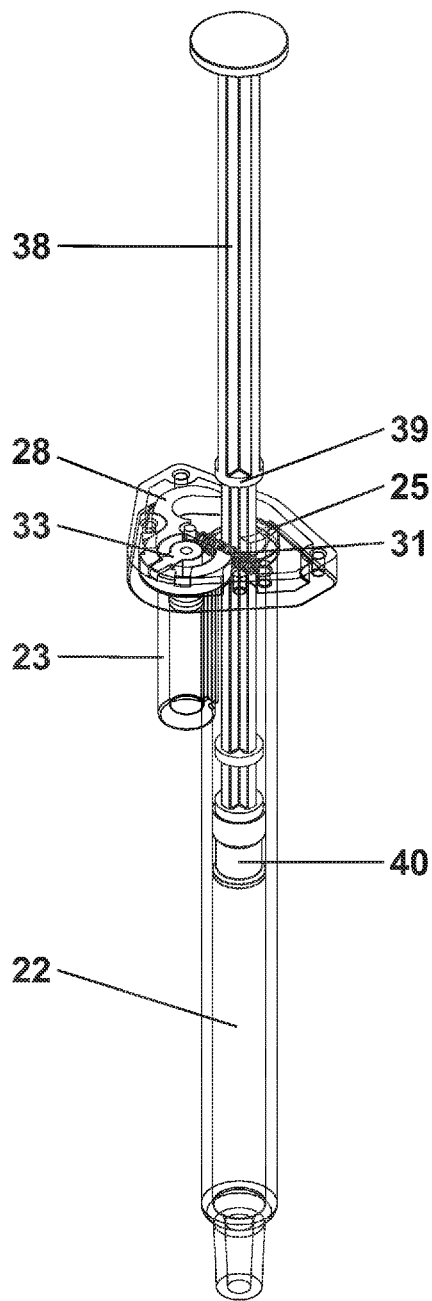
FIG. 7 shows, in perspective, the assembled pre-fillable syringe incorporating a freeze-sensitive locking system with cover removed.

FIG. 7 shows, in perspective, the assembled pre-fillable syringe incorporating a freeze-sensitive locking system with cover removed.

Figure 8:
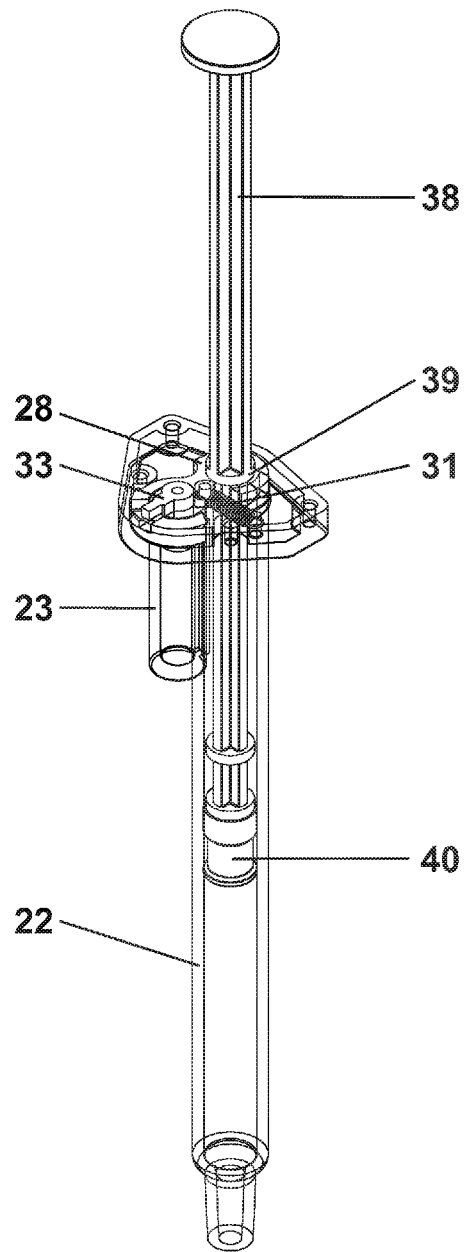
FIG. 8 shows, in perspective, with cover removed, the pre-fillable syringe with the syringe plunger prevented from moving down the syringe barrel by the freeze-sensitive locking system.

FIG. 8 shows, in perspective, with cover removed, the pre-fillable syringe with the syringe plunger prevented from moving down the syringe barrel by the freeze-sensitive locking system.

With reference to FIGS. 5 to 8, a pre-fillable syringe incorporating a freeze-sensitive locking system comprises a syringe barrel 22 with an actuator barrel 23, actuator guide 24, lower plunger rod guide 25, retaining pin 26 and location pin recesses 27. Placed over, and free to rotate about the upper part of the actuator barrel 23 is a latch 28 with locking step 29 and retaining pin 30. Maintaining a clockwise biasing force on the latch 28 is a spring 31 which is secured to the top of the syringe barrel 22 and to the latch 28 by means of the retaining pins 26 and 30. Placed within the actuator barrel 23 is an actuator seal 32 to one end of which is attached an actuator arm 33 which is prevented from rotating relative to the longitudinal axis of the actuator barrel 23 by the actuator guide 24. Secured to the upper surface of the syringe barrel 22 by means of location pins 34 and location pin recesses 27 is a cover 35 with upper plunger rod guide 36 and actuator arm travel recess 37. The syringe plunger assembly comprises a plunger rod 38 with a plunger locking step 39 and a rubber plunger 40.

At assembly, the actuator barrel 23 is filled with a water solution (not shown) and sealed by the actuator seal 32. Clockwise rotation of the latch 28, under the force of the spring 31, is prevented by the actuator arm 33 engaging the locking step 29, thereby enabling the syringe plunger assembly to be passed through the upper plunger rod guide 36, along the lower plunger rod guide 25 and into the syringe barrel 22. The syringe barrel and plunger assembly may now be filled and used in the manner of a conventional syringe, as shown in FIGS. 5 to 7.

Should the contents of the syringe barrel 22 freeze, the water solution contained by the actuator barrel 23, so formulated as to freeze at the same temperature as the contents of the syringe barrel 22, expands, thereby forcing the actuator seal 32 up the actuator barrel 23 and into the actuator arm travel recess 37, disengaging the actuator arm 33 from the locking step 29 and allowing the latch 28 to rotate clockwise, about the longitudinal axis of the actuator barrel 23, under the force of the spring 31, until prevented from further rotating by the plunger rod 38, thus preventing the plunger locking step 39 from passing into the syringe barrel 22 and hence irreversibly preventing the syringe from being used, as shown in FIGS. 5 and 8.

Figure 9:
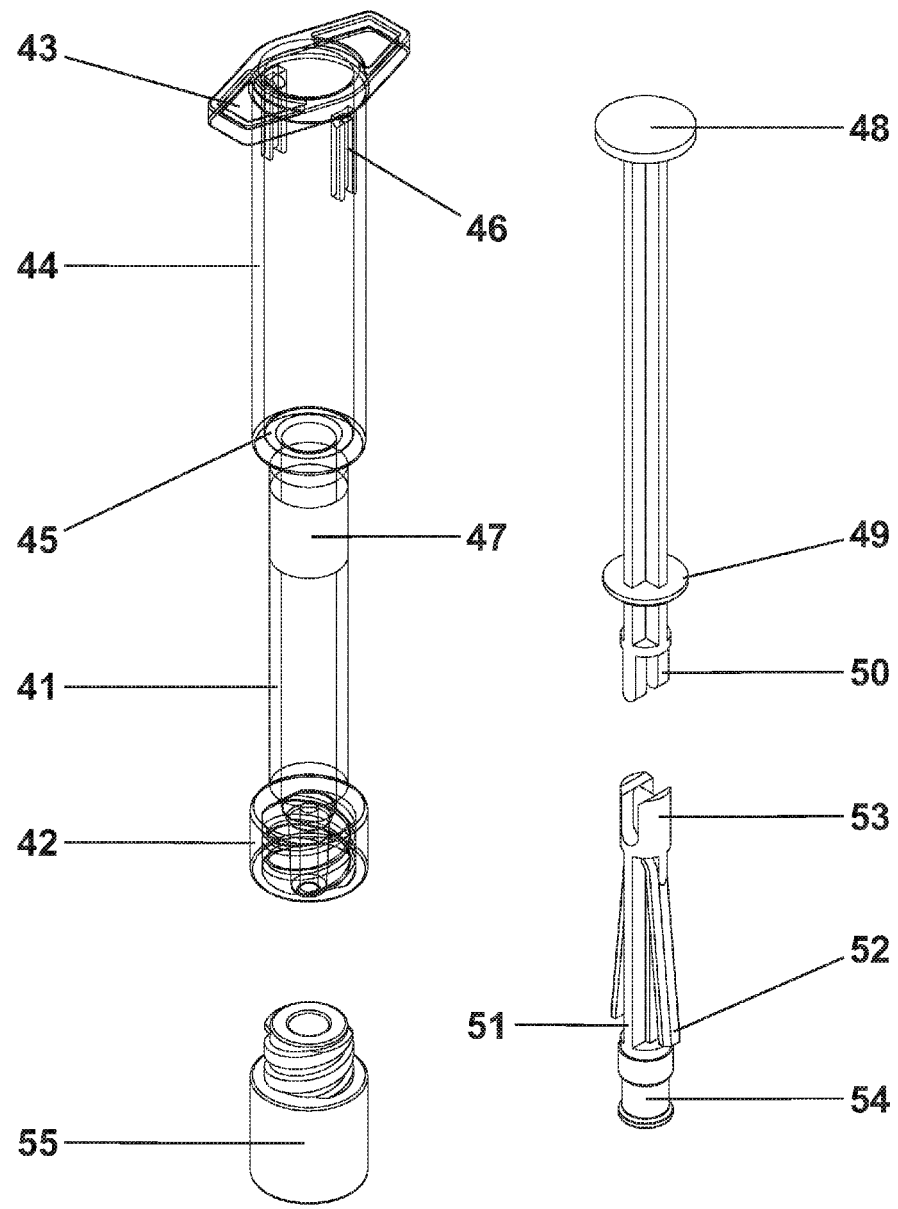
FIG. 9 shows, in perspective, the constituent parts of a luer-lok connector type pre-fillable syringe incorporating a freeze-sensitive locking system.

A third embodiment of the invention will now be described by way of example only with reference to FIGS. 9 to 11 of the accompanying drawings, in which:

FIG. 9 shows, in perspective, the constituent parts of a luer-lok connector type pre-fillable syringe incorporating a freeze-sensitive locking system.

Figure 10:
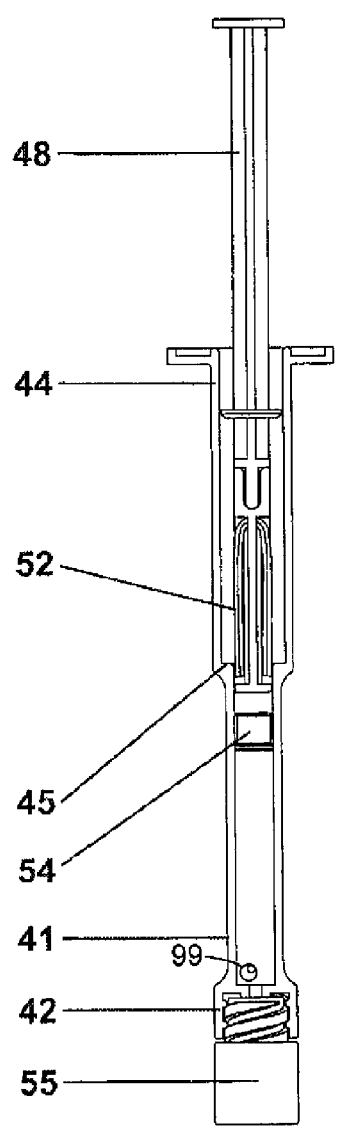
FIG. 10 shows, with syringe barrel in cross-section, the assembled luer-lok connector type pre-fillable syringe incorporating a freeze-sensitive locking system.

FIG. 10 shows, with syringe barrel in cross-section, the assembled luer-lok connector type pre-fillable syringe incorporating a freeze-sensitive locking system.

Figure 11:
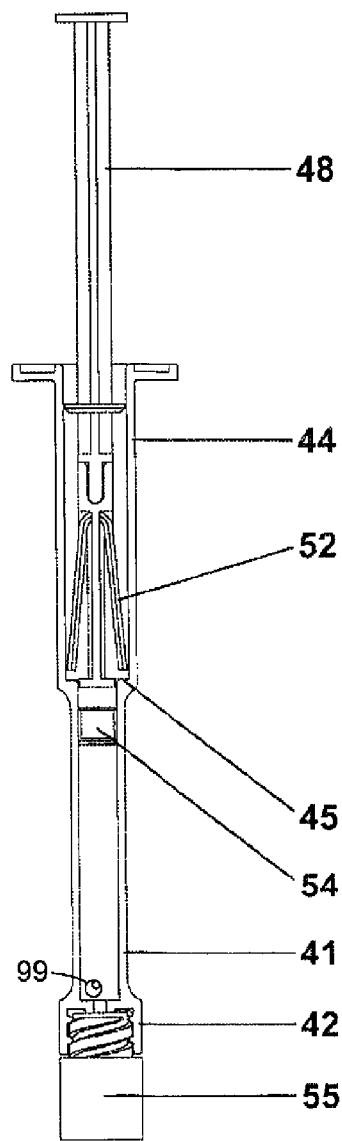
FIG. 11 shows, with syringe barrel in cross-section, the luer-lok connector type pre-finable syringe with the syringe plunger prevented from moving down the syringe barrel by the freeze-sensitive locking system.

FIG. 11 shows, with syringe barrel in cross-section, the luer-lok connector type pre-fillable syringe with the syringe plunger prevented from moving down the syringe barrel by the freeze-sensitive locking system.

With reference to FIGS. 9 to 11, a luer-lok connector type pre-fillable syringe incorporating a freeze-sensitive locking system comprises a syringe barrel 41 with male luer-lok fitting 42, finger tabs 43, upper barrel 44, locking step 45 and upper plunger rod stops 46. Over the syringe barrel 41 is placed an indicator label 47. The syringe plunger assembly comprises an upper plunger rod 48 with upper plunger rod step 49 and upper plunger rod coupling 50 and a lower plunger rod 51 with spring arms 52, lower plunger rod coupling 53 and a plunger 54. A female luer-lock cap 55 is provided to seal the end of the prefilled syringe prior to use.

Upon filling, the syringe barrel 41 is filled with a liquid pharmaceutical formulation containing water (not shown) and sealed by the female luer-lock cap 55. The plunger 54 is positioned in the syringe barrel 41 so that the lower ends of the spring arms 52 on the lower plunger rod 51 rest below the locking step 45 and are deflected inwards by the bore of the syringe barrel 41. To prevent the user from moving the plunger 54 up the syringe barrel 41 and hence releasing the spring arms 52 on the lower plunger rod 51, upper plunger rod coupling 50 and lower plunger rod coupling 53 enable the upper plunger rod 48 to move in a vertical direction, independently of the lower plunger rod 51 until prevented from further movement by the upper plunger rod stops 46. The syringe assembly may now be used in the manner of a conventional pre-fillable syringe as shown in FIGS. 9 and 10.

Should the contents of the syringe barrel 41 freeze, the water in the liquid pharmaceutical formulation expands, forcing the plunger 54 up the syringe barrel 41 until it becomes visible above the indicator label 47 thus indicating to the user that the contents of the syringe have been frozen and should not be used. As the plunger 54 is forced up the syringe barrel 41, the spring arms 52 are released by the syringe barrel 41 and spring outwards into the upper barrel 44 above the locking step 45 thereby irreversibly preventing the lower plunger rod 51 from travelling down the syringe barrel 41 and hence preventing the syringe from being used, as shown in FIGS. 9 and 11.

A fourth embodiment of the invention will now be described by way of example only with reference to FIGS. 12 to 15 of the accompanying drawings, in which:

FIG. 12 shows, in perspective, the constituent parts of a product package consisting of a container with a screw cap incorporating a freeze-sensitive locking system with visual indicator.

FIG. 13 shows, in perspective, the assembled product container.

FIG. 14 shows, in perspective, with outer cap in section, the open product container.

FIG. 15 shows, in perspective, with outer cap in section, the container and screw cap locked together by means of the freeze-sensitive locking system.

With reference to FIGS. 12 to 15, a product package incorporating a freeze-sensitive locking system with visual indicator comprises a container 56 and a screw cap assembly consisting of an outer cap 57 with actuator barrel 58, outer actuator guides 59, indication apertures 60, and vents 61, locked together with, but free to rotate about, an inner cap 62 with inner actuator guides 63 by means of a male rotatable annular snap fit 64 and a female rotatable annular snap fit (not shown). Placed within the actuator barrel 58 is an actuator seal 65 to one end of which is attached an actuator 66 which is prevented from rotating relative to the longitudinal axis of the inner cap 62 by inner actuator guide holes 67. Upper friction stops 68 on the inner cap 62 and lower friction stops 69 on the container 56 are so proportioned as to ensure that the torsional force required to rotate the outer cap 57 about the inner cap 62 is less than the torsional force required to unscrew the female thread (not shown) within the cap assembly about the male thread 70 on the container 56.

At assembly, the actuator barrel 58 is filled with a water solution (not shown) and sealed by the actuator seal 65. The outer actuator guides 59 on the outer cap 57 are located within outer actuator guide slots 71 on the actuator 66 thereby preventing the actuator 66 from rotating relative to the outer cap 57 and enabling the screw cap assembly to be disengaged and re-engaged with the container 56 in the manner of a common screw cap, as shown in FIGS. 12 to 14.

Should the contents of the container 56 freeze, the water solution contained by the actuator barrel 58, so formulated as to freeze at the same temperature as the contents of the container 56, expands, thereby forcing the actuator seal 65 down the actuator barrel 58, disengaging the actuator 66 from the outer actuator guides 59 and allowing the actuator 66 to rotate relative to the outer cap 57 thus irreversibly preventing the cap assembly from being unscrewed from the container 56 and providing, in the indication apertures 60, an indication that the product has been exposed to freezing temperatures, as shown in FIGS. 12 and 15.

Figure 16:
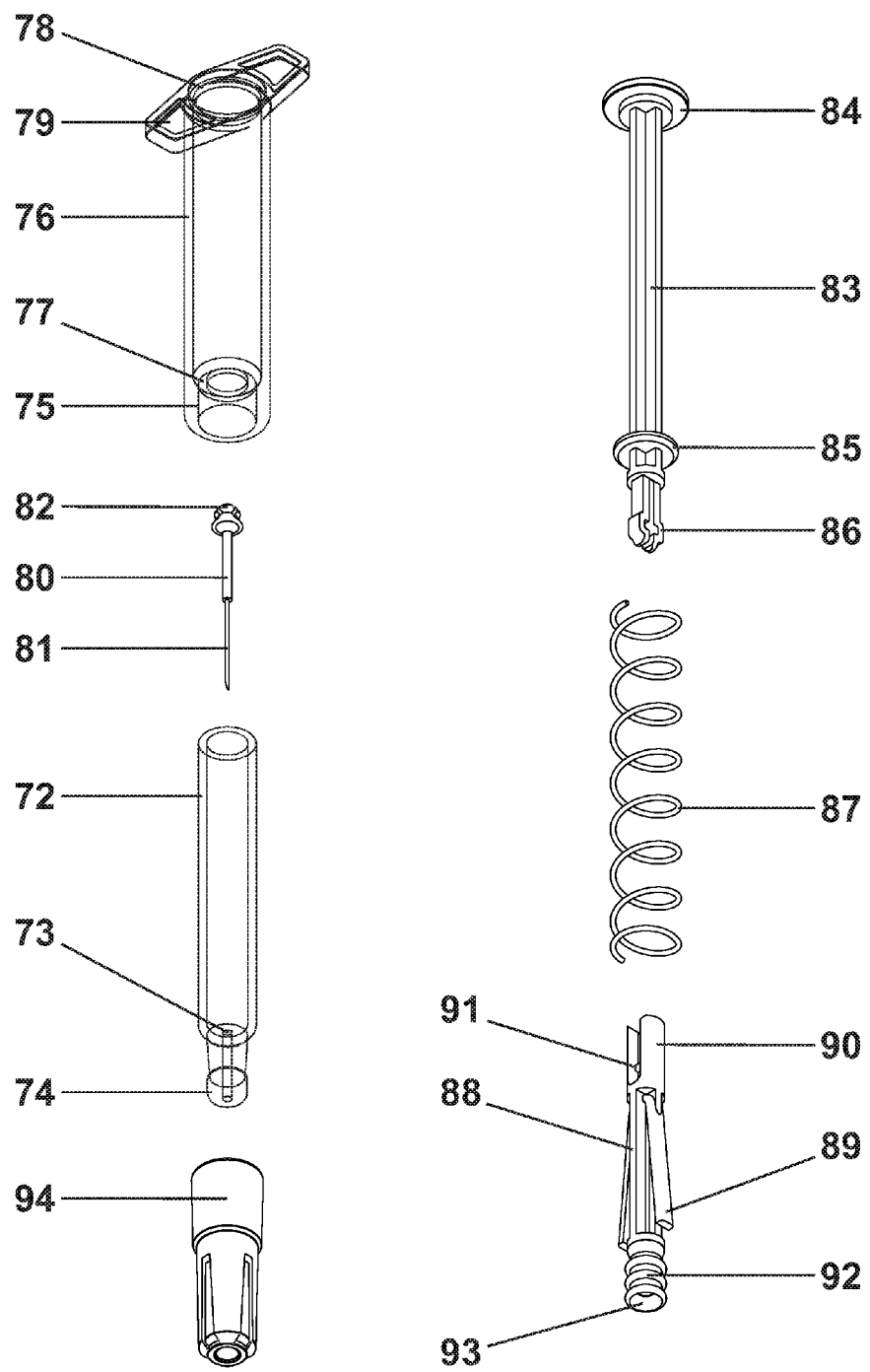
FIG. 16 shows, in perspective, the constituent parts of a pre-fillable syringe incorporating a freeze-sensitive locking system and including a needle retraction system.

A fifth embodiment of the invention will now be described by way of example only with reference to FIGS. 16 to 20 of the accompanying drawings, in which:

FIG. 16 shows, in perspective, the constituent parts of a pre-fillable syringe incorporating a freeze-sensitive locking system and including a needle retraction system.

Figure 17:
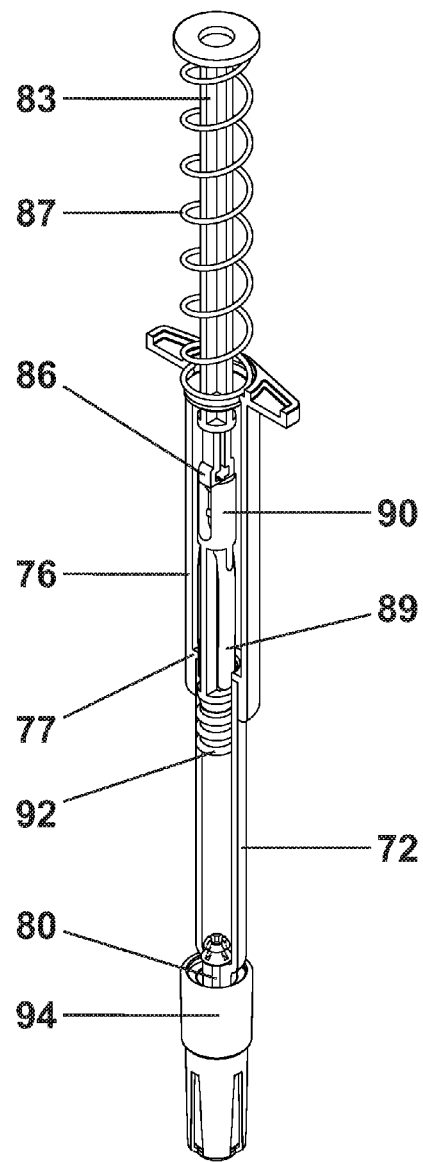
FIG. 17 shows, with upper and lower syringe barrels in cross-section, the assembled pre-finable syringe incorporating a freeze-sensitive locking system and including a needle retraction system.

FIG. 17 shows, with upper and lower syringe barrels in cross-section, the assembled pre-fillable syringe incorporating a freeze-sensitive locking system and including a needle retraction system.

Figure 18:
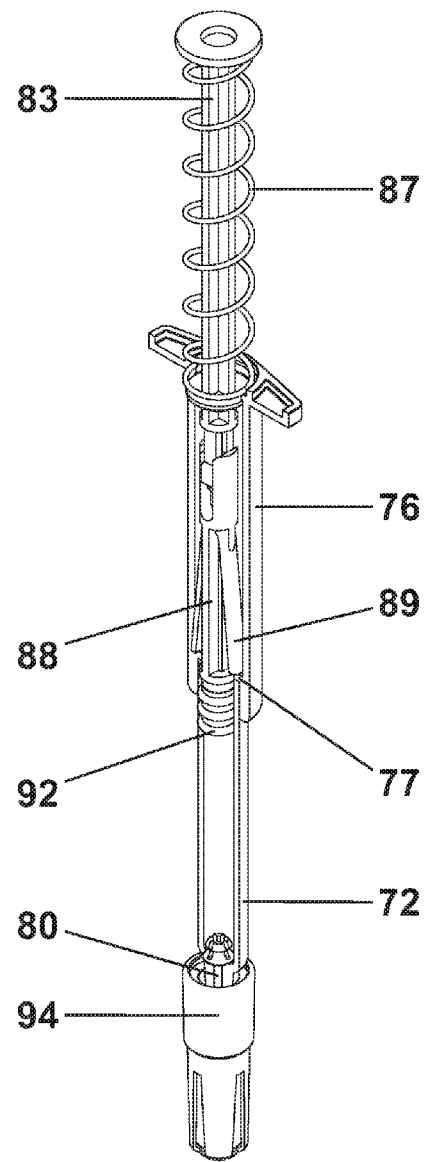
FIG. 18 shows, with upper and lower syringe barrels in cross-section, the pre-fillable syringe with the syringe plunger prevented from moving down the lower syringe barrel by the freeze-sensitive locking system.

FIG. 18 shows, with upper and lower syringe barrels in cross-section, the pre-fillable syringe with the syringe plunger prevented from moving down the lower syringe barrel by the freeze-sensitive locking system.

Figure 19:
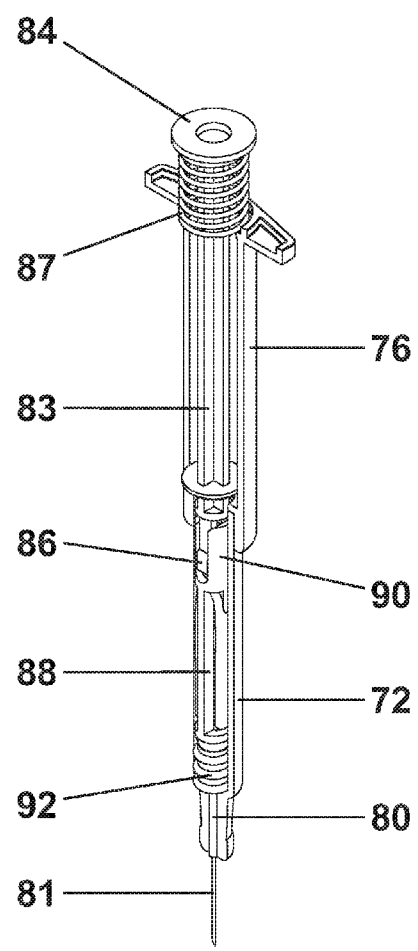
FIG. 19 shows, with upper and lower syringe barrels in cross-section, the pre-fillable syringe with the syringe plunger depressed to its full extent.

FIG. 19 shows, with upper and lower syringe barrels in cross-section, the pre-fillable syringe with the syringe plunger depressed to its full extent.

Figure 20:
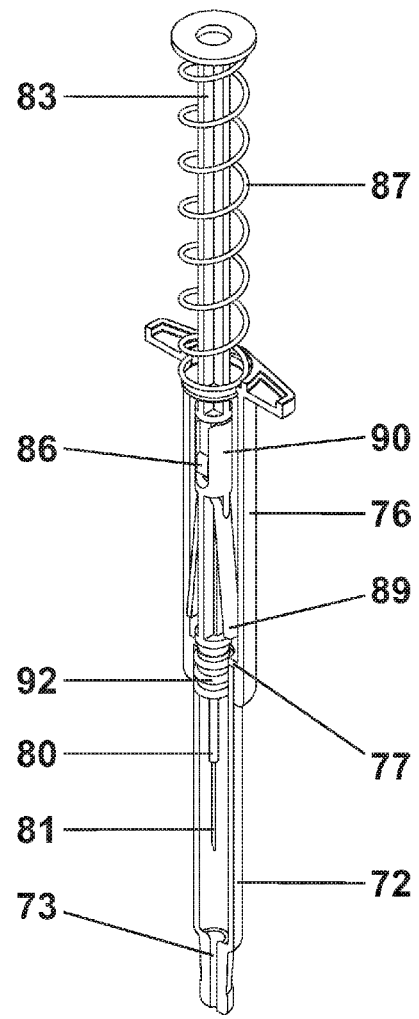
FIG. 20 shows, with upper and lower syringe barrels in cross-section, the pre-fillable syringe with needle retracted.

FIG. 20 shows, with upper and lower syringe barrels in cross-section, the pre-fillable syringe with needle retracted.

With reference to FIGS. 16 to 20, a pre-fillable syringe incorporating a freeze-sensitive locking system and including a needle retraction system comprises a lower syringe barrel 72, with needle assembly guide 73 and needle shield connector 74, attached to the lower barrel seat 75 of an upper syringe barrel 76 with locking step 77, retaining ring 78 and finger tabs 79 and a needle assembly 80 with syringe needle 81 and male snap-fit type connector 82. The syringe plunger assembly comprises an upper plunger rod 83 with thumb rest 84, retaining step 85 and upper plunger rod snap-fit type coupling 86, a spring 87 and a lower plunger rod 88 with spring arms 89, lower plunger rod coupling 90 with locking rib 91 and a plunger 92 with female snap-fit type connector 93. A needle shield 94 which can be removably attached to the needle shield connector 74 is provided to seal the pre-fillable syringe prior to use.

Upon filling, the needle assembly 80 is situated in the needle assembly guide 73 and the lower syringe barrel 72 is filled with a liquid pharmaceutical formulation containing water (not shown). The plunger 92 is positioned in the lower syringe barrel 72 so that the lower ends of the spring arms 89 on the lower plunger rod 88 rest below the locking step 77 on the upper syringe barrel 76 and are deflected inwards by the bore of the lower syringe barrel 72. To prevent the plunger 92 from moving up the lower syringe barrel 72 under the force of the spring 87 and hence releasing the spring arms 89 on the lower plunger rod 88, upper plunger rod snap-fit type coupling 86 and lower plunger rod coupling 90 enable the upper plunger rod 83 to move in a vertical direction independently of the lower plunger rod 88 until prevented from further vertical movement by the retaining step 85 on the upper plunger rod 83 encountering the retaining ring 78 on the upper syringe barrel 76. The syringe assembly is now ready for use as shown in FIGS. 16 and 17.

Should the contents of the lower syringe barrel 72 freeze, the water in the liquid pharmaceutical formulation expands, forcing the plunger 92 up the lower syringe barrel 72. As the plunger 92 is forced up the lower syringe barrel 72, the spring arms 89 are released by the lower syringe barrel 72 and spring outwards into the upper syringe barrel 76 above the locking step 77 thereby preventing the lower plunger rod 88 from travelling down the lower syringe barrel 72 and hence irreversibly preventing the syringe from being used, as shown in FIGS. 16 and 18.

To use the syringe assembly, the needle shield 94 is removed and the thumb rest 84 on the upper plunger rod 83 is depressed thereby compressing the spring 87 and moving the lower plunger rod 88 and hence the plunger 92 down the lower syringe barrel 72 to deliver the liquid pharmaceutical preparation (not shown) through the needle assembly 80. When the plunger 92 has been depressed to its full extent, the male snap-fit type connector 82 on the needle assembly 80 and the female snap-fit type connector 93 on the plunger 92 lock together. A further depression of the upper plunger rod 83 causes the upper plunger rod snap-fit type coupling 86 to ride over the locking rib 91 on the lower plunger rod coupling 90 thus locking the upper and lower plunger rods together. When the thumb rest 84 is released, the upper plunger rod 83, under force of the spring 87, moves in a vertical direction until prevented from further vertical movement by the retaining step 85 encountering the retaining ring 78 on the upper syringe barrel 76. As the needle assembly 80 is locked to the plunger 92 and the lower plunger rod 88 is locked to the upper plunger rod 83, the needle assembly 80 is retracted into the lower syringe barrel 72. When the needle assembly 80 is retracted into the lower syringe barrel 72, the spring arms 89 on the lower plunger rod 88 are released by the lower syringe barrel 72 and spring outwards into the upper syringe barrel 76 above the locking step 77 thereby preventing the lower plunger rod 88 from travelling down the lower syringe barrel 72 and hence preventing the needle assembly 80 from travelling down the needle assembly guide 73 thus preventing the syringe needle 81 from being exposed as shown in FIGS. 16, 19 and 20.

The invention claimed is:

1. A device containing a freeze-sensitive liquid containing a pharmaceutical or medical product suitable for use in therapy or diagnosis, the device comprising a first part containing the freeze-sensitive liquid, a second part which engages the first part and allows, or can be disengaged or displaced to allow, the liquid to be dispensed or utilised, a locking means for irreversibly preventing the freeze-sensitive liquid from being dispensed, and a freeze-sensitive activator for the locking means, wherein the freezing of an aqueous liquid engages the locking means, whereby thawing of the aqueous liquid will not reverse the locking means.

2. The device according to claim 1, which also includes an indicator of the state of the locking means.

3. The device according to claim 1, wherein the first part is a syringe barrel.

4. The device according to claim 3, wherein the freeze-sensitive liquid comprises the aqueous liquid, whereby expansion of the aqueous liquid in the syringe barrel activates the locking means.

5. The device according to claim 4, which includes a means to facilitate mixing of the freeze-sensitive liquid prior to administration.

6. The device according to claim 3, wherein the syringe barrel includes a luer-lock, luer-slip or other type of connector to enable a closure to be attached to an end of the syringe barrel which can be removed to allow a syringe needle to be attached to an end of the first part prior to use.

7. The device according to claim 3, wherein the syringe barrel has an attached needle.

8. The device according to claim 3, which includes a means to prevent re-use of the a syringe integral with the second part.

9. The device according to claim 8, wherein the means to prevent re-use is a needle retraction system.

10. The device according to claim 3, which includes a means to prevent a needle stick injury integral with the second part.

11. The device according to claim 10, wherein the means to prevent a needle stick injury is a needle retraction system.

12. A device containing a freeze-sensitive liquid, the device comprising:
   a compartment containing the freeze-sensitive liquid;
   a delivery system integral with the compartment comprising a mechanical structure that disperses the freeze-sensitive liquid;
   a locking mechanism that disables the delivery system; and
   an aqueous liquid proximate to the locking mechanism, wherein the locking mechanism is actuated by a change in a physical property of the aqueous liquid.

13. The device of claim 12, wherein the locking mechanism is integral with the delivery system.

* * * * *